United States Patent [19]

Kaneko

[11] Patent Number: 4,883,784
[45] Date of Patent: Nov. 28, 1989

[54] HUMAN COMPLEMENT FACTORS AND THEIR THERAPEUTIC USE

[75] Inventor: Isao Kaneko, Tokyo, Japan

[73] Assignee: Sankyo Company Limited, Tokyo, Japan

[21] Appl. No.: 181,309

[22] Filed: Apr. 13, 1988

Related U.S. Application Data

[63] Continuation of Ser. No. 927,733, Nov. 5, 1986, abandoned.

[30] Foreign Application Priority Data

Nov. 8, 1985 [JP] Japan ................. 60-250187

[51] Int. Cl.4 .................... A61K 37/04; A61K 37/43
[52] U.S. Cl. .................................... 514/8; 424/94.63; 424/94.65; 424/94.66; 424/94.67; 514/2; 514/21; 530/380; 530/392; 530/393; 530/394; 530/413; 530/829; 530/830; 530/831
[58] Field of Search ................. 424/101, 94.63, 94.65, 424/94.66, 94.67; 514/2, 8, 21; 530/350, 380, 392, 393, 394, 413, 829, 830, 831, 400

[56] References Cited

U.S. PATENT DOCUMENTS 4,308,204 12/1981 Becker et al. ................ 530/413 X
4,444,757 4/1984 Strausser ............................ 514/21
4,618,494 10/1986 Angers ............................... 424/101

OTHER PUBLICATIONS

Immune Complex Disease in Experimental Animals and Man, Adv. Immunology 16 (1973), 186-204, C. G. Cochrane, D. Koffler.
A Spontaneous Rheumatoid Arthritis-Like Disease in MRL/1 Mice, J. Ex. Ped. 155, pp. 1690-1701, 1982, LeMing Hang, Argyrios N. Theofilopoulos, and Frank J. Dixon.
Alternative Pathway of Complement, Adv. Immunology, 29 (1-53) 1980, Hans J. Muller-Eberhard & Robert D. Schreiber.
Generation of Three Different Fragments of Bound C3 Wtih Purified Factor I or Serum, J. Immunology 129, pp. 2051-2060, 1982, Gordon D. Ross, John D. Lambris et al.
Biochem. J. (1982) vol. 203, pp. 293-298, Purification of Human C3b Inactivator by Monoclonal-Antibody Affinity Chromatography, Li-min Hsiung et al.
Proc. Natl. Acad. Sci. U.S.A. vol. 73, No. 9, pp. 3268-3272, Sep. 1976-Control of the Amplification Convertase of Complement by the Plasma Protein β1H-John M. Weiler et al.
J. Exp. Med., vol. 148, pp. 1198-1215 (1978)-Spontaneous Murine Lupus-Like Syndromes-Brian S. Andrews et al.
J. Immunol., vol. 119, No. 4, pp. 1248-1252 (1977), Purification of C3b Inactivator and Demonstration of its Two Polypeptide Chain Structure-Douglas T. Fearon.
Biochem. J., vol. 191, pp. 173-182 (1980), Purification of the Human Complement Control Protein C3b Inactivator, L. Gail Crossley and Rodney R. Porter.
J. Immunol., vol. 125, pp. 578-582 (1980)-Cleavage of C4b by C3b Inactivator: Production of a Nicked Form of C4b, C4b', as an Intermediate Cleavage Product of C4b by C3b Inactivator-Shigeharu Nagasawa et al.
J. Exp. Med., vol. 144, pp. 1147-1163 (1976), Modulation of the Alternative Complement Pathway by β1H Globulin, Keith Whaley and Shaun Ruddy.

Primary Examiner—Howard E. Schain
Attorney, Agent, or Firm—Frishauf, Holtz, Goodman & Woodward

[57] ABSTRACT

The administration of Factor I and/or Factor H to a mammal has been found to alleviate or prevent such autoimmune diseases as systemic lupus erythematosus, rheumatoid arthritis and glomerulonephritis.

9 Claims, 1 Drawing Sheet

HUMAN COMPLEMENT FACTORS AND THEIR THERAPEUTIC USE

This is a continuation of application Ser. No. 927,733 filed Nov. 5, 1986, now abandoned.

BACKGROUND TO THE INVENTION

This invention relates to human complement Factor I and Factor H, both of which have now been found to be effective for the therapy of autoimmune diseases.

Antibody-antigen complexes are generated when antibodies bind to their specific alloantigens or autoantigens in vivo. Most of these complexes react with serum complement componets (C1, C4, C2 and C3), and thus so-called "immune complexes", consisting of antigen, antibody and the complement components including C3b, are generated. These immune complexes further interact with C5-C9 components, generating a membrane attack complex, C5b-C9, and an anaphylatoxin C5a, one of the most potent chemical mediators of inflammation. Moreover, such immune complexes are often deposited on the inside surfaces of blood vessels and also in the connective tissues around the vessels. These sequential events eventually cause inflammatory reactions and tissue damage.

On the other hand, there is a metabolic process for inactivating such active immune complexes. Factor I, one of the complement regulatory proteins, can inactivate C3b molecules in the immune complexes by converting the C3b to C3bi or C3d in co-operation with Factor H, C4b-binding protein and the complement receptors (CR1, CR2 and CR3) on erythrocytes and phagocytes. The immune complexes bearing such C3bi and C3d cannot further activate C5-C9 components and are eventually processed and cleared, mainly by the hepatic tissues. The level of immune complexes in the blood, therefore, is the result of a balance between the processes resulting in their generation and their inactivation (degradation).

Factors H and I and the ability of endogenous Factors H and I to inactivate C3b molecules in the normal course of the mammalian metabolism are known. Indeed, Factor I was hitherto known as "C3b inactivator" (="C3bINA") or "C4b inactivator" [see e.g. Hsiung et al. Biochem. J. (1982) 203, 293–298]. Factor H was hitherto known as "$\beta$1H" [see e.g. Weiler et al. Proc. Natl. Acad. Sci. USA 73, 3268–3272 (1976)]. However, their value in the treatment of autoimmune diseases has not hitherto been suspected, nor has any casual connection between Factors H and I and such autoimmune diseases as systemic lupus erythematosus (SLE), rheumatoid arthritis (RA) and glomerulonephritis been proved or suggested.

These autoimmune diseases, such as SLE, RA and glomerulonephritis, that are not effectively cured by current conventional therapy are considered to be vascular diseases, and we believe that they are mainly caused by the deposition of immune complexes inside and outside the blood vessels of various tissues, although the precise mechanism of the deposition of these immune complexes has not yet been elucidated. Recently, an inverse relationship between the frequency of occurrence of SLE and the genetically controlled density of complement receptor 1 (CR1) on erythrocytes (sites/cells) has been suggested. This also suggests that the occurrence and exacerbation of SLE is, at least in part, due to a reduced capability to process or inactivate the immune complexes. However, it is not possible to explain every such occurrence or exacerbation only by CR1 sites on erythrocytes, because (1) about 40% of SLE patients have normal levels of CR1 sites (2) about 12% of normal subjects have low levels of CR1 sites (3) there are not differences in CR1 sites between the exacerbation and regression stages in the same SLE patients.

We have been searching for factors other than CR1 to correlate with the occurrence and exacerbation of SLE and have now found that the complement components Factor I and Factor H, both of which are essential for the inactivation of immune complexes, decreased in the preor early phases of the exacerbation stage, but not during most of the regression stage. This suggests that the temporary decrease in Factor I and/or Factor H may be one cause of the accumulation of immune complexes that exacerbate the clinical conditions of SLE patients.

BRIEF SUMMARY OF INVENTION

The present invention is thus based upon the discovery that the administration of exogenous Factor H and/or Factor I to a mammalian, e.g. human, patient suffering from one or more of the autoimmuen diseases, especially SLE, RA and glomerulonephritis, will cure or alleviate the symptoms of that disease.

In accordance with the present invention, there is, therefore, provided a method of treating a mammal suffering from an autoimmune disease by administering to said mammal an effective amount of a complement factor selected from the group consisting of Factor H, Factor I and mixtures of Factor H and Factor I.

DETAILED DESCRIPTION OF INVENTION

Figure 1:
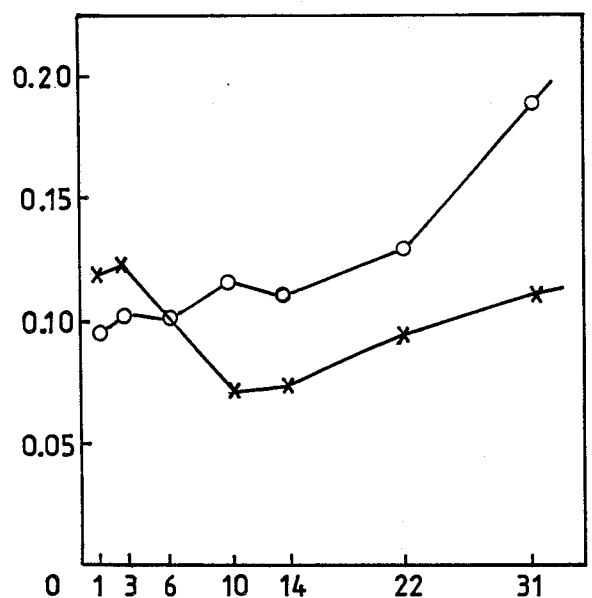
FIG. 1 is a graph showing the variation of urinary protein levels (ordinate) against time in days (abscissa) in mice suffering from spontaneous autoimmune diseases, one group (shown by "x" on the graph) having been given a single administration of Factor H and the other group (shown by "o" on the graph) being a control.

The effects of Factors I and H on autoimmune diseases were investigated by administering these compounds to an animal suffering spontaneous autoimmune diseases. As a result, Factor I and/or Factor H were demonstrated to have a potent therapeutic and preventive effect on the autoimmune diseases in this animal. The test animals used were mice of the MRL/lpr strain. These animals develop spontaneously a group of symptoms closely resembling those of human SLE, RA and glomerulonephritis. They are commonly recognized as providing a model for the investigation and treatment of these autoimmune disorders in humans and other mammals [see e.g. Andrews et al. J. Exp. Med. 148, 1198–1215 (1978)].

We have found that the so-called active immune complexes which develop the autoimmune diseases are inactivated by the administration of exogenous Factor I and/or Factor H. Factor I and Factor H are known to be present in blood plasma, and can be separated and purified by a combination of several methods. For example, Factor I can be purified to homogeneity from fresh human plasma by column chromatography using lysine-Sepharose, QAE-Sephadex, C3b-Sepharose and Sephadex G-150 (SEPHAROSE and SEPHADEX are trade marks). In addition, Factor I can be purified from human plasma by using an agarose column coupled with a mouse monoclonal anti-I antibody. Factor H can be purified to homogeneity from fresh human plasma by using lysine-sepharose, QAE-Sephadex, DEAE-Toyopearl, Sephacryl S-300 and hydroxyapatite column chromatography (TOYOPEARL and SEPHACRYL are trade marks). It is also possible to obtain Factor I and/or Factor H by using genetic engineering in which the complementary and/or genomic DNA for Factor I and/or Factor H are expressed in, for example, E. Coli, yeast, actinomyces or mammalian cells.

Full details of the separation and purification of Factor I (C3bINA) and Factor H ($\beta$B1H) are given by Fearon [J. Immunol. 119, 1248–1252 (1977)], Crossley et al. [Biochem. J. (1980) 191, 173–182], Nagasawa et al. [J. Immunol. 125, 578–582 (1980)], Weiler et al. [Proc. Natl. Acad. Sci. USA 73, 3268–3272 (1976)] and Whaley et al. [J. Exp. Med. 144, 1147–1163 (1976)], the disclosures of which are incorporated herein by reference.

Factors H and I are preferably employed in the present invention in a form free (or essentially or substantially free) from native blood plasma contaminants (such as transferrin, plasmin, IgG or Factor B) so as to have consistent and predictable physical and biochemical properties. However, as noted hereafter, other exogenous materials may be added to the pharmaceutical formulation containing Factor H and/or I, if desired, to achieve particular results.

Factors I and H are preferably administered in the form of a solution in saline or phosphate buffered saline (PBS). If desired, human transferrin and/or serum albumin (as stabilizer) may be added to these preparations of Factor I and/or Factor H. Although these factors can be administered orally or non-orally, non-oral administration, such as intravenous injection, is preferred. The dosage of the drug will depend on the age, clinical conditions and body weight of the patients as well as the nature and severity of the disorder. In general, Factor I or Factor H is given in a dose of from 50 to 1000 mg or of from 50 to 6000 mg, respectively, daily for an adult human. This may administered in a single dose or in divided doses.

Although Factor I and/or Factor H itself can be administered directly as the preventive and therapeutic drug for autoimmune diseases, it is preferred to administer them in association with various known pharmaceutical carriers, diluents or adjuvants appropriate to the formulation, e.g. capsules or injections. With regard to the toxicity of Factor I and Factor H, the $LD_{50}$ values on intravenous injection in mice were greater than 2 g/kg and 3 g/kg, respectively.

EXPERIMENT 1

Effects of Factor I and/or Factor H on mice with autoimmune diseases

MRL/lpr mice with spontaneous autoimmune diseases were used in this experiment. Since these mice began to show proteinuria with ageing due to the renal glomerular defect that is induced by the deposition of the immune complexes on the glomeruli, their pathological conditions were judged by the protein contents of their urine. Factor I and Factor H, used in this experiment, had been purified to homogeneity as assessed by electrophoresis in the presence of SDS (sodium dodecyl sulfate).

Twelve weeks old MRL/lpr mice were divided into four groups (5 mice per group), designated as groups #1, #2, #3 and #4. Factor I dissolved in PBS was administered intravenously to the mice of group #2 at a dosage of 6 mg/kg once every four days for 4 weeks. Factor H dissolved in PBS was administered intravenously to the mice of group #3 at a dosage of 100 mg/kg at the same intervals. Factor I and Factor H, dissolved in PBS, were administered intravenously to the mice of group #4 at dosages of 6 and 100 mg/kg, respectively, at the same intervals. To the mice of group #1 (control), only PBS was administered intravenously as above. One day after the final administration, each group of mice was maintained for 24 hours in metabolic cages, and the urine was collected. Urinary protein levels were determined by using a protein assay kit produced by Bio-Rad Laboratories of Richmond, California, USA, using bovine serum albumin as the standard protein. The following Table shows the urinary protein levels (mg protein/24 hours/5 mice) of these four groups. As shown, compared with the control (group #1), there were marked decreases in the urinary protein levels in groups #2, #3 and #4. Thus, Factor I, Factor H and the mixture of these factors were all effective in improving or preventing the proteinuria that represents the pathological conditions of the autoimmune diseases.

TABLE

| Group | Urinary protein levels mg/24 hours/5 mice |
| --- | --- |
| 1. Control | 14.9 |
| 2. Administration of Factor I | 9.7 |
| 3. Administration of Factor H | 7.4 |
| 4. Administration of Factors I and H | 6.5 |

EXPERIMENT 2

Therapeutic effect of a single administration of factor H on the proteinuria of MRL/lpr mice 16 weeks old MRL/lpr mice that had already manifested nephritis were divided into two groups (5 mice per group), designated as groups #1 and #2, and housed in separate cages. On day 1, each group of mice was maintained for 17 hours in metabolic cages and their urine was collected. On day 2, Factor H dissolved in PBS was administerd intravenously to the mice of group #2 at a dosage of 8 mg/kg. To the mice of group #1 (control), only PBS was administered intravenously. On days 6, 10, 14, 22 and 31, the urine of each group was collected by maintaining the mice for 17 hours in metabolic cages as above. Urinary protein levels were determined by using a protein assay kit produced by Bio-Rad Laboratories as described in Experiment 1. FIG. 1 shows the urinaryprotein levels (mg protein/hour/mouse)of the two groups. The results of the group #1 are marked "o" whilst those of group #2 are marked "x". As shown, a single administration of Factor H strongly and time-dependently reduced the urinary protein levels in group #2, and this reduction was maintained for about 20 days. In contrast, the control mice in group #1, to which only PBS was administered, time-dependently increased their urinary protein levels.

EXPERIMENT 3

Effect of Factor I on renal glomerular function for filtration in MRL/lpr mice.

Figure 2:
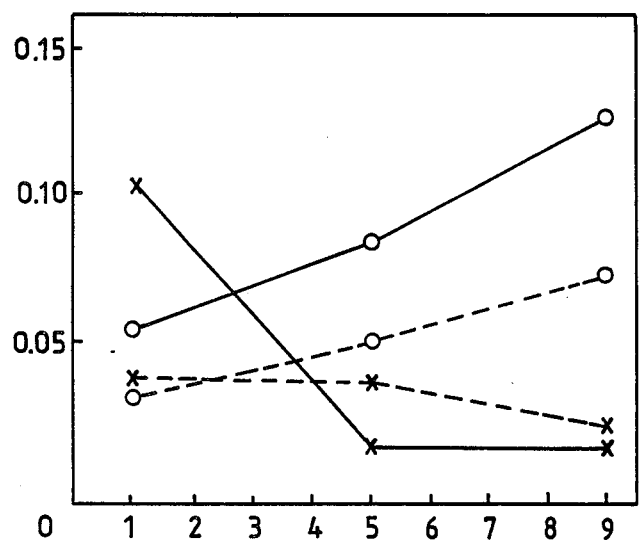
FIG. 2 is a graph similar to FIG. 1 but showing the effect of Factor I.

23 weeks old MRL/lpr mice that had already manifested nephritis were divided into two groups (5 mice per group), designated groups #1 and #2, and then housed in separate cages. On days 2 and 6, PBS alone and Factor I dissolved in PBS at a dosage of 1 mg/kg were administered to the mice in groups #1 and #2, respectively. On days 1, 5 and 9 after administration, each group of mice was maintained for 17 hours in metabolic cages and their urine was collected as above. Total urinary protein levels were determined by using a protein assay kit produced by Bio-Rad Laboratories as described in experiment 1. In addition, the urinary protein of each group was analyzed by SDS-polyacrylamide gel electrophoresis. After staining the gel with coomassie brilliant blue and de-staining with methanol-acetic acid solution, the amounts of protein in each band in the gel were determined by a densitometer (CS-900-30, Shimazu). From the amounts of total urinary protein and of fractionated protein bands on the gel, the amounts of urinary proteins of higher (more than 40K) and lower (less than 40K) molecular weight were calculated. FIG. 2 shows the amounts of urinary proteins (mg protein/hour/mouse) with the higher and lower molecular weight of the two groups of mice. The amounts of higher molecular weight protein are shown by a solid line; the amounts of lower molecular weight protein are shown by a dotted line. As is Experiment 2, the results of group #1 are marked "o" and those of group #2 are marked "x". As shown, the administration of factor I strongly and time-dependently reduced the amounts of urinary protein especially in the higher molecular weight fractions (mainly consisting of MW 68K protein) that are present in MRL/lpr mice with severe glomerulonephritis, without affecting the amounts of lower molecular weight fractions (mainly consisting of NW 14K and 22K proteins). Thus, Factor I was effective in improving the renal glomerular function for filtration. On the other hand, administration of PBS alone did not inhibit a time-dependent increase of the urinary protein levels with higher molecular weight, leading to the renal glomerular defect in MRL/lpr mice. It is well known that normal glomeruli in the kidney can filter only proteins of MW less than 40K.

I claim:

1. A method of treating a mammal suffering from a disease selected from the group consisting of systemic lupus erythematosus, rheumatoid arthritis and glomerulonephritis by administering to said mammal an effective amount of a complement factor selected from the group consisting of Factor H, Factor I and mixtures of Factor H and Factor I.

2. The method as claimed in claim 1, wherein said complement factor is Factor H alone.

3. The method as claimed in claim 1, wherein said complement factor is Factor I alone.

4. The method as claimed in claim 1, wherein said complement factor is a mixture of Factors H and I.

5. The method as claimed in claim 1, wherein said complement factor is administered parenterally.

6. The method as claimed in claim 5, wherein said administration is by intravenous injection.

7. The method as claimed in claim 1, wherein from 50 to 1,000 mg of Factor I are administered daily.

8. The method as claimed in claim 1, wherein from 50 to 6,000 mg of Factor H are administered daily.

9. The method as claimed in claim 1 wherein said complement factor is an exogenous factor selected from the group consisting of Factor H, Factor I and mixtures of Factor H and Factor I free or essentially free from native blood plasma contaminants.

* * * * *